(12) United States Patent
Kwon et al.

(10) Patent No.: US 10,813,561 B2
(45) Date of Patent: Oct. 27, 2020

(54) TOUCH-TYPE BLOOD PRESSURE MEASUREMENT APPARATUS AND METHOD

(71) Applicant: SAMSUNG ELECTRONICS CO., LTD., Suwon-si (KR)

(72) Inventors: Yong Joo Kwon, Yongin-si (KR); Jae Min Kang, Seoul (KR); Youn Ho Kim, Hwaseong-si (KR); Seung Woo Noh, Seongnam-si (KR); Sang Yun Park, Hwaseong-si (KR); Young Zoon Yoon, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 460 days.

(21) Appl. No.: 15/680,821

(22) Filed: Aug. 18, 2017

(65) Prior Publication Data
US 2018/0177413 A1   Jun. 28, 2018

(30) Foreign Application Priority Data

Dec. 27, 2016   (KR) ................... 10-2016-0180132

(51) Int. Cl.
*A61B 5/021*   (2006.01)
*G06F 3/044*   (2006.01)
(Continued)

(52) U.S. Cl.
CPC ........ *A61B 5/02108* (2013.01); *A61B 5/0053* (2013.01); *A61B 5/022* (2013.01);
(Continued)

(58) Field of Classification Search
CPC .............. A61B 5/02108; A61B 5/0053; A61B 5/02055; A61B 5/022; A61B 5/0261;
(Continued)

(56) References Cited

U.S. PATENT DOCUMENTS 6,492,979 B1 * 12/2002 Kent ..................... G06F 3/0414
                                                                178/18.01
8,761,853 B2   6/2014 Thaveeprungsriporn et al.
(Continued)

FOREIGN PATENT DOCUMENTS

CN    106923807 A  *  7/2017
EP     0694283 A2      1/1996
(Continued)

OTHER PUBLICATIONS

Translation of Lin Ke et al. (Chinese Pub. No. CN 106923807 A, Jul. 7, 2017).*
(Continued)

*Primary Examiner* — Carolyn A Pehlke
(74) *Attorney, Agent, or Firm* — Sughrue Mion, PLLC

(57) ABSTRACT

A touch-type blood pressure measurement apparatus is provided. The touch-type blood pressure measurement apparatus include: a touch sensor configured to generate a contact area signal when a finger of a user is in contact with the touch sensor; at least one photoplethysmogram (PPG) sensor configured to generate a PPG signal of the user while the finger is in contact with the touch sensor; a force sensor configured to generate a touch force signal of the finger in contact with the touch sensor; and a controller configured to obtain a blood pressure of the user based on the contact area signal, the PPG signal, and the touch force signal.

20 Claims, 27 Drawing Sheets

(51) Int. Cl.
*A61B 5/0205* (2006.01)
*A61B 5/00* (2006.01)
*A61B 5/1172* (2016.01)
*A61B 5/022* (2006.01)
*A61B 5/026* (2006.01)
*G06F 3/041* (2006.01)
*G06K 9/00* (2006.01)
*A61B 5/024* (2006.01)
*A61B 90/00* (2016.01)

(52) U.S. Cl.
CPC ........ *A61B 5/02055* (2013.01); *A61B 5/0261* (2013.01); *A61B 5/1172* (2013.01); *A61B 5/6826* (2013.01); *A61B 5/6843* (2013.01); *A61B 5/6898* (2013.01); *A61B 5/7278* (2013.01); *A61B 5/742* (2013.01); *G06F 3/044* (2013.01); *A61B 5/02427* (2013.01); *A61B 2090/065* (2016.02); *A61B 2562/0238* (2013.01); *A61B 2562/0247* (2013.01); *A61B 2562/0252* (2013.01); *A61B 2562/046* (2013.01); *A61B 2562/063* (2013.01); *G06F 3/0416* (2013.01); *G06F 2203/04105* (2013.01); *G06K 9/0002* (2013.01)

(58) Field of Classification Search
CPC ... A61B 5/1172; A61B 5/6826; A61B 5/6843; A61B 5/6898; A61B 5/7278; A61B 5/742; G06F 3/044
See application file for complete search history.

(56) References Cited

U.S. PATENT DOCUMENTS

| | | |
|---|---|---|
| 8,870,781 B2 | 10/2014 | Lee et al. |
| 9,072,439 B2 | 7/2015 | Kassim et al. |
| 9,226,671 B2 | 1/2016 | Cho et al. |
| 9,232,915 B2 | 1/2016 | Chua et al. |
| 9,289,177 B2 | 3/2016 | Kassim et al. |
| 9,480,407 B2 | 11/2016 | Kumar et al. |
| 9,538,927 B2 | 1/2017 | Thaveeprungsriporn et al. |
| 2012/0190944 A1 | 7/2012 | Thaveeprungsriporn et al. |
| 2013/0296665 A1 | 11/2013 | Kassim et al. |
| 2013/0296666 A1 | 11/2013 | Kumar et al. |
| 2013/0296673 A1 | 11/2013 | Thaveeprungsriporn et al. |
| 2013/0296714 A1 | 11/2013 | Kassim et al. |
| 2015/0011900 A1 | 1/2015 | Lu et al. |
| 2015/0051500 A1 | 2/2015 | Elliott et al. |
| 2015/0062078 A1 | 3/2015 | Christman et al. |
| 2015/0157262 A1* | 6/2015 | Schuessler ........... A61B 5/0261 600/479 |
| 2015/0374249 A1 | 12/2015 | Elliott et al. |
| 2016/0015301 A1 | 1/2016 | Elliott et al. |
| 2016/0198955 A1 | 7/2016 | Fortin |
| 2017/0172476 A1* | 6/2017 | Schilthuizen ......... A61B 5/024 |
| 2017/0251935 A1* | 9/2017 | Yuen .................... A61B 5/7278 |
| 2017/0367597 A1 | 12/2017 | Fortin |
| 2018/0199893 A1* | 7/2018 | Hubner ................ A61B 5/7282 |
| 2018/0344193 A1* | 12/2018 | Gui ....................... H04M 1/725 |

FOREIGN PATENT DOCUMENTS

| | | |
|---|---|---|
| JP | 3940150 B2 | 7/2007 |
| JP | 2007-202693 A | 8/2007 |
| JP | 2007-209374 A | 8/2007 |
| JP | 2007-244600 A | 9/2007 |
| JP | 2009-66042 A | 4/2009 |
| JP | 2009-201895 A | 9/2009 |
| JP | 4796025 B2 | 10/2011 |
| JP | 5027604 B2 | 9/2012 |
| JP | 2013-031597 A | 2/2013 |
| JP | 2014-507209 A | 3/2014 |
| JP | 2015-192702 A | 11/2015 |
| JP | 2016-146994 A | 8/2016 |
| KR | 10-0660349 B1 | 12/2006 |
| KR | 10-0681387 B1 | 2/2007 |
| KR | 10-1167614 B1 | 7/2012 |
| KR | 10-2014-0022493 A | 2/2014 |
| KR | 10-2014-0058521 A | 5/2014 |
| KR | 10-1421698 B1 | 8/2014 |
| KR | 10-2015-0119913 A | 10/2015 |
| WO | 2012/099535 A1 | 7/2012 |
| WO | 2016/110781 A1 | 7/2016 |

OTHER PUBLICATIONS

Communication dated Apr. 9, 2018 by the European Patent Office in counterpart European Patent Application No. 17193614.9.

* cited by examiner

CONTACT AREA

TOUCH-TYPE BLOOD PRESSURE MEASUREMENT APPARATUS AND METHOD

CROSS-REFERENCE TO RELATED APPLICATION(S)

This application claims priority from Korean Patent Application No. 10-2016-0180132, filed on Dec. 27, 2016 in the Korean Intellectual Property Office, the entire disclosure of which is incorporated herein by reference for all purposes.

BACKGROUND

1. Field

Apparatuses consistent with the present disclosure relate to an apparatus for measuring a blood pressure, and more particularly, to a technology for measuring a blood pressure in a cuffless manner.

2. Description of Related Art

A pressurized cuff-based method is used for general blood pressure measurement. The pressurized cuff-based method is a non-continuous measurement method in which a cuff is used to tighten blood vessels up to the maximum blood pressure and loosen to measure a blood pressure. The pressurized cuff-based method is difficult to apply to a portable device due to the configuration of a pressurizing pump or the like.

Recently, a blood pressure measurement apparatus employing non-pressurized cuffless method for measuring a blood pressure without using a cuff has been studied. For example, there is a pulse transit time (PTT)-based blood pressure measurement apparatus and method that estimate a blood pressure using pulse wave velocity. In another example, there is a pulse wave analysis (PWA)-based blood pressure measurement apparatus and method that estimate a blood pressure by analyzing pulse wave form.

The PTT method is disadvantageous in that it is necessary to perform correction for each individual for accurate measurement and it is difficult to construct a compact device because bio-signals must be measured at two or more positions in order to measure the pulse wave velocity. Because the PWA method estimates a blood pressure only by analyzing the pulse wave form, it is disadvantageously vulnerable to noise and has a limitation in accurate blood pressure measurement.

SUMMARY

Example embodiments address at least the above problems and/or disadvantages and other disadvantages not described above. Also, the example embodiments are not required to overcome the disadvantages described above, and may not overcome any of the problems described above.

According to an aspect of an example embodiment, there is provided touch-type blood pressure measurement apparatus including: a touch sensor configured to generate a contact area signal when a finger of a user is in contact with the touch sensor; at least one photoplethysmogram (PPG) sensor configured to generate a PPG signal of the user while the finger is in contact with the touch sensor; a force sensor configured to generate a touch force signal of the finger in contact with the touch sensor; and a controller configured to obtain a blood pressure of the user based on the contact area signal, the PPG signal, and the touch force signal.

The controller may be further configured to determine a contact pressure based on the contact area signal and the touch force signal and obtain the blood pressure of the user based on a change of the PPG signal according to the contact pressure.

The controller may be further configured to generate a contact pressure profile according to a contact region based on the contact area signal and the touch force signal, and correct a contact pressure exerted on a blood vessel of the user based on the contact pressure profile.

The at least one PPG sensor may include a plurality of PPG sensors arranged in an array.

The controller may be further configured to obtain a PPG signal from one of the plurality PPG sensors placed at a contact center among the plurality of PPG sensors, based on a contact location signal generated by the touch sensor.

The controller may be configured to obtain the PPG signals from the plurality of PPG sensors in a time-division manner.

The touch-type blood pressure measurement apparatus may further include a display configured to display a contact pressure of the finger in contact with the touch sensor and a guide for the user to apply the contact pressure in a predetermined pattern to the touch sensor.

The touch-type blood pressure measurement apparatus may further include a temperature sensor configured to generate a temperature signal of the finger in contact with the touch sensor.

The controller may be further configured to correct the PPG signal according to the temperature signal generated by the temperature sensor.

The touch sensor may further configure to obtain fingerprint information of the user, and the controller may be further configured to identify the user based on the fingerprint information.

The controller may be further configured to correct the blood pressure according to previously input information about at least one of a height, a weight, and an age of the user.

The touch-type blood pressure measurement apparatus may further include a contact pressure adjuster configured to adjust a contact pressure applied to the touch sensor by the finger.

The controller may be further configured to control the contact pressure adjuster so that the contact pressure is applied to the touch sensor in a predetermined pattern.

The contact pressure adjuster may include a piezoelectric actuator or a voice coil motor.

According to an aspect of another example embodiment, there is provided touch-type blood pressure measurement apparatus including: a photoplethysmogram (PPG) sensor having a contact area which is touched with a finger of the user, the PPG sensor being configured to generate a PPG signal of the user while the finger is in contact with the contact area; a force sensor configured to generate a touch force signal of the finger in contact with the contact area; and a controller configured to obtain a blood pressure of the user based on the PPG signal, the touch force signal, and predetermined contact area information regarding the contact area.

The controller may be further configured to determine a contact pressure based on the predetermined contact area information and the touch force signal, and determine a blood pressure of the user based on a change of the PPG signal according to the contact pressure.

The touch-type blood pressure measurement apparatus may further include a contact pressure adjuster configured to adjust a contact pressure of the finger applied to the contact area by the finger.

According to an aspect of another example embodiment, there is provided touch-type blood pressure measurement apparatus including: a photoplethysmogram (PPG) sensor configured to generate a PPG signal of a user while a finger of the user is in contact with the PPG sensor; a contact pressure adjuster configured to adjust a contact pressure applied to the PPG sensor by the finger; and a controller configured to continuously obtain a blood pressure of the user by controlling the contact pressure adjuster to adjust the contact pressure and analyzing a change of the PPG signal according to adjustment of the contact pressure.

The controller may be further configured to continuously obtain a blood pressure of the user based on the contact pressure that is adjusted by the contact pressure adjuster to cancel out the PPG signal measured from the PPG sensor.

According to an aspect of another example embodiment, there is provided a touch-type blood pressure measurement apparatus including: a touch sensor configured to generate a contact area signal when a finger of a user is in contact with the touch sensor; a force sensor configured to generate a touch force signal of the finger in contact with the touch sensor; and a controller configured to obtain a blood pressure of the user based on the contact area signal and the touch force signal.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
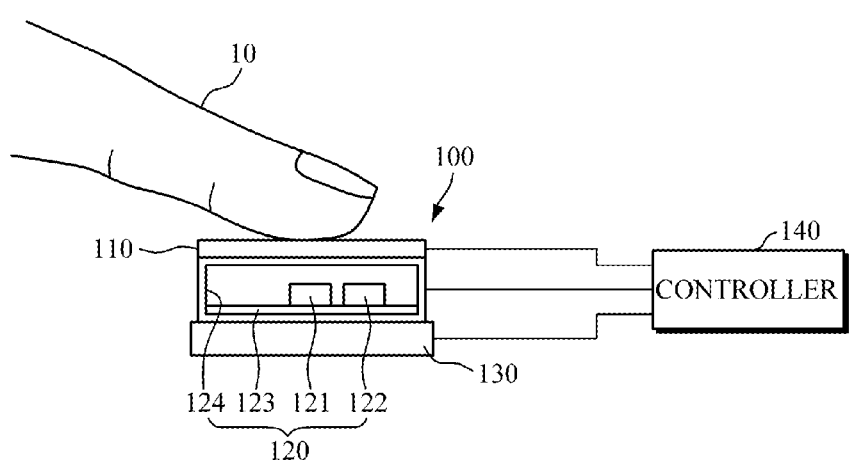
FIG. 1 is a diagram illustrating a configuration of a touch-type blood pressure measurement apparatus according to a first example embodiment.

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Throughout the drawings and the detailed description, unless otherwise described, the same drawing reference numerals will be understood to refer to the same elements, features, and structures. The relative size and depiction of these elements may be exaggerated for clarity, illustration, and convenience.

Advantages and features of the present invention and methods of accomplishing the same may be understood more readily by reference to the following detailed description of example embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the inventive concept will only be defined by the appended claims.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise.

In the specification, unless explicitly described to the contrary, the terms "comprise" and "includes", and variations such as "comprises," "comprising," "includes" and "including" will be understood to imply the inclusion of stated elements but not the exclusion of any other elements. Terms such as " . . . unit" and "module" denote units that process at least one function or operation, and they may be implemented by using hardware (e.g., a microprocessor or an integrated circuit), software, or a combination of hardware and software.

Hereinafter, example embodiments of a touch-type blood pressure measurement apparatus will be described in detail with reference to the accompanying drawings. The touch-type blood pressure measurement apparatus of the example embodiments may be mounted in a hardware or software module for wearable devices, terminals, such as a smartphone, a tablet personal computer (PC), a desktop PC, and a notebook PC, and medical devices. Alternatively, the touch-type blood pressure measurement apparatus may be implemented in various modified example embodiments, such as being implemented as an independent hardware device.

Figure 2:
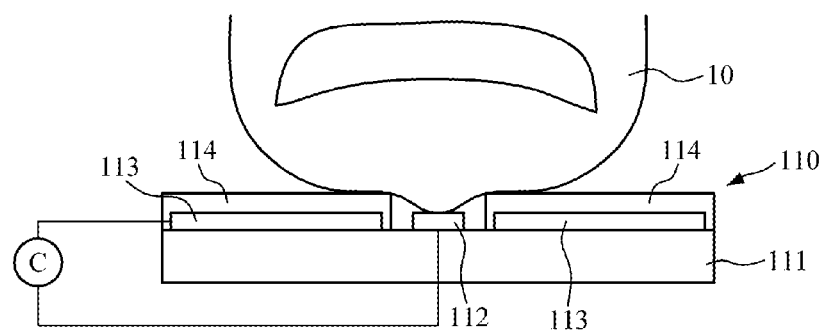
FIG. 2 is a cross-sectional view of an example of a touch sensor.

FIG. 1 is a diagram illustrating a configuration of a touch-type blood pressure measurement apparatus according to a first example embodiment. FIG. 2 is a cross-sectional view of an example of a touch sensor.

Referring to FIGS. 1 and 2, the touch-type blood pressure measurement apparatus 100 according to the first example embodiment includes a touch sensor 110, a photoplethysmogram (PPG) sensor 120, a force sensor 130, and a controller 140.

The touch sensor 110 senses a contact area when a user touches the touch sensor 110 with a finger 10 to generate a contact area signal indicative of the contact area. The PPG sensor 120 measures a PPG of the user in a state where the finger 10 is in contact with the touch sensor 110 to generate a PPG signal. The force sensor 130 may senses a touch force when the finger 10 is in contact with the touch sensor 110 to generate a touch force signal. The controller 140 obtains the user's blood pressure based on the contact area signal, the PPG signal, and the touch force signal.

The touch-type blood pressure measurement apparatus 100 is capable of measuring an accurate blood pressure based on the contact area information obtained by the touch sensor 110, as well as the PPG information obtained by the PPG sensor 120 and the touch force information obtained by the force sensor 130. That is, the contact area of the finger 10 in contact with the touch sensor 110 may vary not only according to the touch force but also according to the shape of the finger 10, so that an accurate blood pressure may be measured by calculating an accurate contact pressure through simultaneous measurement of the touch force and the contact area.

For example, the touch sensor 110 may be disposed on an outermost portion of the touch-type blood pressure measurement apparatus 100 so the user's finger 10 may easily contact the touch sensor 110. The touch sensor 110 is disposed above the PPG sensor, based on a case where the user touches from above the touch sensor 110 with a finger 10 of the user. The PPG sensor 120 measures the PPG signal by transmitting light to and receiving light reflected from the finger 10 in contact with the touch sensor 110, and hence the touch sensor 110 has optical transparency. Therefore, the touch sensor 110 may transmit the light emitted from the PPG sensor 120 to the finger 10 and transmit the light reflected from the tissue of the finger 10 to the PPG sensor 120.

As shown in FIG. 2, the touch sensor 110 is configured as a capacitive sensor and may measure the contact area signal of the finger 10. The touch sensor 110 includes a transparent substrate 111, a first transparent electrode 112 and a second transparent electrode 113 which are spaced apart from each other on the transparent substrate 111, and a transparent cover 114 which covers a top portion of the second transparent electrode 113 while exposing the first transparent electrode 112.

The transparent substrate 111 may be formed of transparent plastic or transparent glass to have optical transparency and an insulation property. The transparent substrate 111 supports the first and second transparent electrodes 112 and 113.

The first and second transparent electrodes 112 and 113 may be made of a transparent conductive material, such as, indium tin oxide (ITO) or a carbon nanotube, and formed on the transparent substrate 111. The first transparent electrode 112 may be disposed on a center portion of the transparent substrate 111 and the second transparent electrode 113 may be disposed on a peripheral portion of the transparent substrate 111 in such a manner that the second transparent electrode 113 surrounds the first transparent electrode 112. The first and second transparent electrodes 112 and 113 may be each formed with a constant thickness. The first transparent electrode 112 may function as a ground electrode and the second transparent electrode 113 may function as a sensing electrode.

The transparent cover 114 may be formed of transparent plastic or transparent glass and has optical transparency and conductivity. The transparent cover 114 may protect the second transparent electrode 113. The transparent cover 114 may be attached to the transparent substrate 111 by an adhesive layer while covering the second transparent electrode 113. The transparent cover 114 may be formed to cover a top portion of the first transparent electrode 112 as well as the second transparent electrode 113, thereby protecting the first transparent electrode 112.

The touch sensor 110 measures a contact area of the finger 10 in the following manner. In a standby state in which the first and second transparent electrodes 112 and 113 are supplied with a sensing current, when the user touches a top portion of the transparent cover 114 including the first transparent electrode 112 with a finger of the user, a capacitance between the first transparent electrode 112 and the second transparent electrode 113 changes according to the contact of the finger 10 which has a capacitance.

In this case, an amount of change in capacitance depends on a size of the contact area of the finger 10. As the contact area of the finger in contact with the touch sensor 110 increases, the current flowing into the finger 10 increases, and thus the amount of change in the capacitance between the first transparent electrode 112 and the second transparent electrode 113 is increased. As the contact area of the finger 10 in contact with the touch sensor 110 decreases, the current flowing into the finger 10 decreases, and thus the amount of change in the capacitance between the first transparent electrode 112 and the second transparent electrode 113 is reduced. The contact area of the finger 10 according to the amount of change in the capacitance may be obtained using a preset correlation model indicating a correlation between the contact area of a finger and the amount of change in the capacitance.

Signals output from the first transparent electrode 112 and the second transparent electrode 113 may be processed by a signal processor dedicated for a touch sensor and provided to the controller 140. When the signal processor receives the signals from the first transparent electrode 112 and the second transparent electrode 113, the signal processor performs preprocessing, such as noise removal from the received signals, signal amplification, or the like. For example, the signal processor may perform preprocessing, such as detrending by which a signal is normalized and a trend and an offset are removed from the signal, signal smoothing, high-frequency noise removal using a low pass filter, or the like. In addition, if the received signal is an analog signal, the signal processor may convert the analog signal into a digital signal.

The controller 140 provides the sensing current to the first and second transparent electrodes 112 and 113. In this state, when the user touches the touch sensor 110 with a finger 10 of the user, the controller 140 may obtain the contact area of the finger 10 according to the amount of change in the capacitance using the previously stored correlation model indicating the correlation between the contact area of a finger and the amount of change in the capacitance. The correlation model may be implemented as a mathematical algorithm, but is not limited thereto, and may be implemented in a matching table and stored in a storage device.

In this case, the storage device may include a flash memory, a hard disk, and a micro multimedia card, a card-type memory (e.g., SD, XD memory, or the like), random access memory (RAM), static random access memory (SRAM), read-only memory (ROM), electrically erasable programmable read-only memory (EEPROM), programmable read-only memory (PROM), magnetic memory, a magnetic disk, an optical disk, and the like, but is not limited thereto.

For example, the PPG sensor 120 is disposed below the touch sensor 110 based on a case where the user touches from above the touch sensor 110 with a finger 10 of the user. The PPG sensor 120 may include one light source 121 and one photodetector 122 so as to measure a PPG signal of the user. Alternatively, a plurality of light sources 121 and photo detectors 122 may be provided.

The light source 121 emits light to the tissue of the finger 10 of the user. The photodetector 122 detects light returning from the tissue of the user which is irradiated by the light source 121. The light source 121 may be configured to emit infrared light. The light source 121 may include a light emitting diode, a laser diode, or a fluorescent substance to emit infrared light, but is not limited thereto. The photodetector 122 may be formed by a photo diode. The light source 121 and the photodetector 122 may be mounted on a circuit substrate 123 and then accommodated in a housing 124. The housing 124 may be formed such that a surface thereof facing the touch sensor 110 transmits light.

A PPG is a waveform that reflects the change of vascular volume in peripheral parts according to the heartbeat. The blood that is released from the left ventricle in the systolic phase is transferred to the peripheral tissues, so the blood volume of the artery is increased. In addition, red blood cells carry more oxyhemoglobin to the peripheral tissues in the systolic phase of the heart. In the diastolic phase, the blood partially flows from the peripheral tissues into the heart. When light is emitted to the peripheral veins, the light is absorbed by the peripheral tissues.

The light absorbance is dependent on a hematocrit and the blood volume. The light absorbance has a maximum value in the systolic phase of the heart, and has a minimum value in the diastolic phase of the heart. The PPG signal reflects the maximum value of the light absorbance in the systolic phase of the heart, and reflects the minimum value of the light absorbance in the diastolic phase of the heart. In addition, the PPG signal may appear to oscillate with the heart cycle period. Therefore, the PPG signal reflects the change of blood pressure according to the heartbeat, and thus it can be used for blood pressure measurement.

The PPG sensor 120 is controlled by the controller 140. The signal output from the photodetector 122 may be processed by the signal processor dedicated for the PPG sensor and then provided to the controller 140. When the signal processor receives the PPG signal from the photodetector 122, the signal processor performs preprocessing, such as noise removal from the received signal, signal amplification, or the like, and may convert the received signal into a digital signal if the received signal is an analog signal.

When the user touches the touch sensor 110 with a finger 10, the controller 140 controls the light source 121 to emit light to the finger 10 and controls the photodetector 122 to detect light returning from the tissue of the finger 10. The controller 140 takes into account a PPG signal detected by the photodetector 122 when measuring a blood pressure.

For example, the force sensor 130 is disposed below the PPG sensor 120 based on a case where the user touches from above the touch sensor 110 with the finger 10. The force sensor 130 measures a touch force transferred through the touch sensor 110 and the PPG sensor 120 when the finger 10 is in contact with the touch sensor 110. The force sensor 130 may be configured in various ways, such as a load cell.

The signal output from the force sensor 130 is processed by the signal processor dedicated for the force sensor and then is transmitted to the controller 140. When receiving the signal from the force sensor 130, the signal processor performs preprocessing, such as noise removal from the received signal, signal amplification, and the like, and may convert the received signal into a digital signal if the signal is an analog signal.

For example, the controller 140 may be a device capable of computing, such as a microprocessor. The controller 140 calculates a contact pressure based on the contact area signal and the touch force signal. In this case, the controller 140 may calculate a mean contact pressure by dividing a touch force value by a contact area value. In addition, the controller 140 may obtain the user's blood pressure by analyzing a change of the PPG signal according to the calculated contact pressure, which will be described with reference to FIGS. 3 and 4A to 6B.

Figure 3:
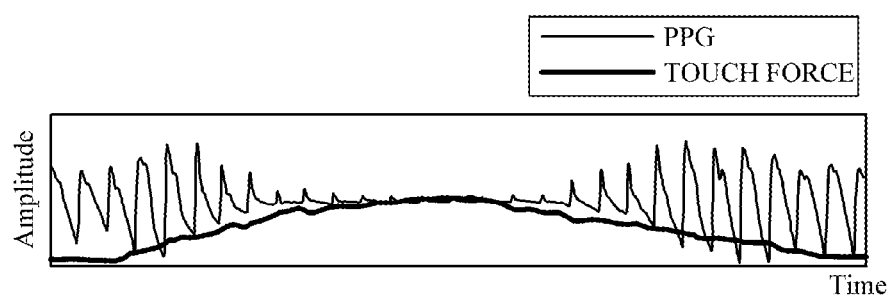
FIG. 3 and FIGS. 4A to 6C are diagrams for describing blood pressure measurement process.

When the user touches and removes the finger 10 from the touch sensor 110, the touch force gradually increases and gradually decreases after reaching the maximum value. The PPG signal according to the change of the touch force may have the form as shown in FIG. 3.

As illustrated in FIGS. 4A to 6C, the contact area of the finger 10 contacting the touch sensor 110 varies depending on the touch force. A contact pressure (CP), which is obtained based on the touch force and the contact area, is applied around a blood vessel 11. In addition, the PPG sensor 120 outputs a PPG signal according to the contact pressure CP.

Figure 4A:
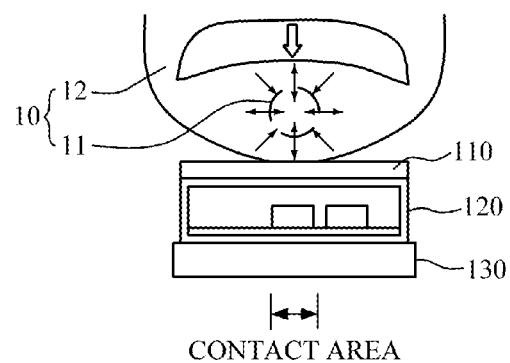
Figure 4B:
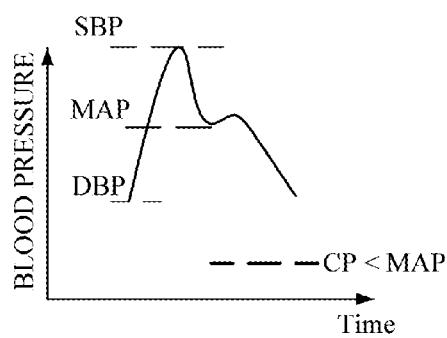
Figure 4C:
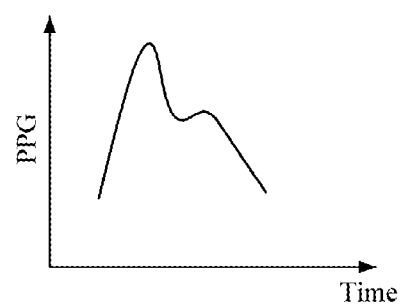

As illustrated in FIGS. 4A to 4C, the blood vessel 11 has a diastolic blood pressure (DBP), a systolic blood pressure (SBP), and a mean arterial pressure (MAP). When the CP is smaller than an MAP, an elastic restoring force of tissue 12 acts in the direction of compressing the blood vessel 11, and hence the amplitude of the PPG signal becomes smaller than that of the PPG signal shown in FIG. 5C.

Figure 5A:
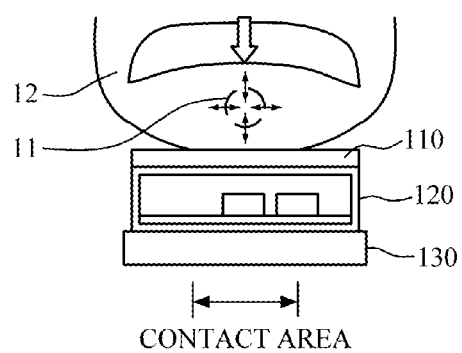
Figure 5B:
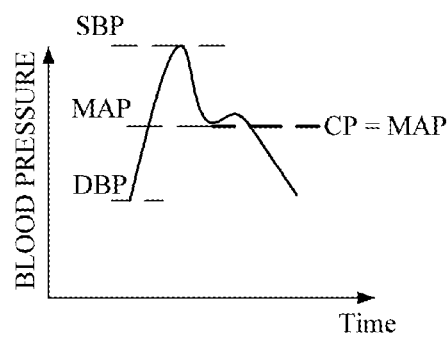
Figure 5C:
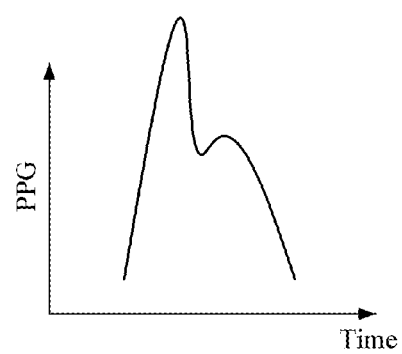

As illustrated in FIGS. 5A to 5C, when the CP is equal to the MAP, the elastic restoring force of the tissue 12 becomes zero and hence does not affect the blood vessel 11, so that the amplitude of the PPG signal is maximized.

Figure 6A:
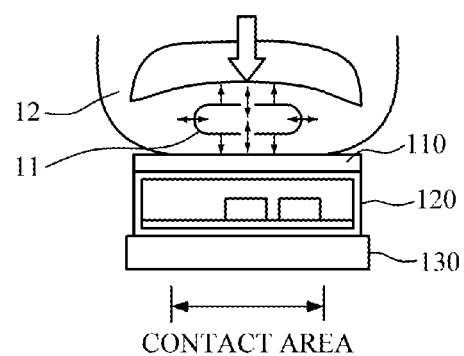
Figure 6B:
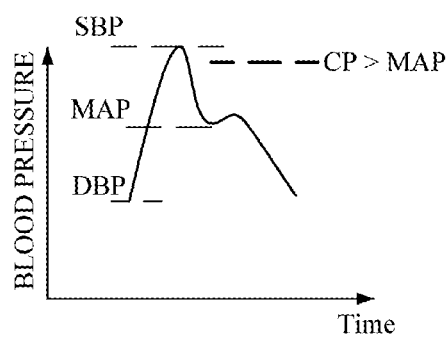
Figure 6C:
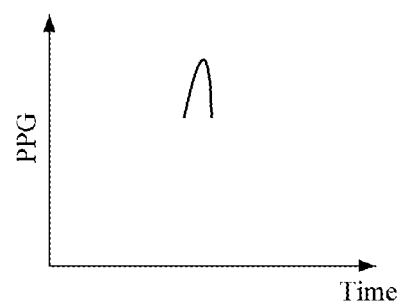

As illustrated in FIGS. 6A to 6C, when the CP is greater than the MAP, the elastic restoring force of the tissue 12 acts in the direction of expansion of the tissue 11, so that the amplitude of the PPG signal becomes smaller than that of the PPG signal shown in FIG. 5C.

Therefore, the controller 140 may analyze the change of the PPG signal according to the CP and estimate that the CP corresponding to the PPG signal having the maximum amplitude is the MAP. In addition, the controller 140 may analyze the change of the PPG signal according to the CP and estimate the DBP and the SBP. In this case, the controller 140 may set a blood pressure estimation interval which includes the maximum amplitude, and average the CP in the set blood pressure estimation interval or average the CP by applying a weight.

As described above, the contact area of the finger 10 in contact with the touch sensor 110 may vary according to the touch force or the shape of the finger 10. An accurate contact pressure is obtained by simultaneously measuring the touch force and the contact area, thereby realizing accurate blood pressure measurement.

Figure 7:
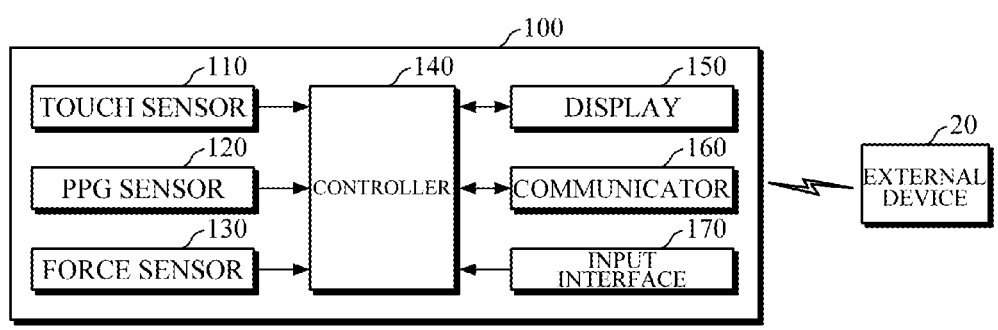
FIG. 7 is a block diagram illustrating an example in which the touch-type blood pressure measurement apparatus shown in FIG. 1 further includes a display and a communicator.

As illustrated in FIG. 7, the touch-type blood pressure measurement apparatus 100 may further include a display 150 and a communicator 160.

Figure 8:
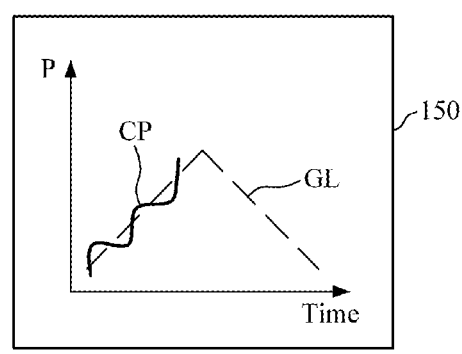
FIG. 8 is a graph for describing an example of an operation of the display of FIG. 7.

The display 150 may display the contact pressure of the touch sensor 110 in contact with the finger 10 to guide the user to apply a contact pressure of a predetermined pattern to the touch sensor 110. For example, as shown in FIG. 8, the display 150 displays a guideline GL on a contact time axis and a contact pressure axis. The guideline GL increases linearly and decreases linearly after reaching the maximum value.

When the user touches and removes a finger 10 of the user from the touch sensor 110 for blood pressure measurement, the display 150 displays the varying CP in a graph on the contact time axis and the contact pressure axis. Accordingly, the user is able to touch the touch sensor 110 with the finger 10 while paying attention to ensure that the CP displayed on a screen of the display 150 does not deviate from a set range along the guideline GL. As a result, more accurate blood pressure measurement may be performed.

Figure 9:
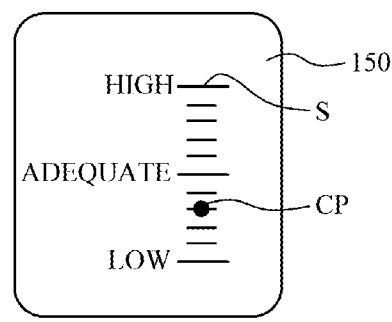
FIG. 9 is a diagram for describing another example of an operation of the display.

In another example, as illustrated in FIG. 9, the display 150 may display the CP on a scale S of high, adequate, and low on the screen.

In addition to the blood pressure information, the display 150 may display additional information, such as warning or alarm, according to blood pressure information so as to provide it to the user. For example, when a dangerous level of blood pressure is extracted, it may be represented by a red color, and on the contrary, when a normal level of blood pressure is extracted, it may be represented by a green color. The display 150 may include a touch input function, by which the user may input various commands, and the display 150 may output a user interface for performing necessary operations. In addition, an input interface 170 may be provided to receive a user's control command and transmit the control command to the controller 140. The input interface 170 may include a power button for the user to input a command for power on/off of the touch-type blood pressure measurement apparatus 100.

The communicator 160 is a communication interface that includes a transmitter and receiver, and may access a communication network by utilizing a communication technology under the control of the controller 140 and may transmit and receive necessary data to/from an external device 20 connected to the same communication network. The controller 140 may control the communicator 160 to establish a connection with the external device 20 and process various operations in cooperation with the external device 20. In this case, the controller 140 may provide necessary information, such as the measured contact area signal, a PPG signal, a touch force signal, and extracted blood pressure information according to cardiovascular feature extraction related functions of the external apparatus 20 associated with the controller 140.

The communication technology may include Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, 3G communication, 4G communication, 5G communication, or the like, but is not limited thereto.

When the blood pressure is extracted, the controller 140 may transmit the extracted blood pressure information to the external device 20 through the communicator 160 so that the external device 20 can provide the information to the user through an interface module included in the external device 20, such as a speaker, a display, a haptic device, or the like. In this case, the external device 20 may be a mobile device which has superior computing performance to the touch-type blood pressure measurement apparatus 100 and can be carried by the user, such as a smartphone, a tablet PC, or the like. However, the external device 20 is not limited thereto, and may include various information providing devices, such as a desktop PC, a notebook PC, and the like.

In another example, when the external device 20 has superior computing performance and provides a function for extracting a blood pressure using a contact area signal, a PPG signal, and a touch force signal, the communicator 160 may transmit the signals to the external device 20 under the control of the controller 140 so as to allow the external device 20 to perform blood pressure extraction. In this case, the external device 20 may be a device with a blood pressure extraction function, such as a smartphone, a table PC, a desktop PC, a notebook PC, a server, or the like.

The external device 20 may extract a blood pressure when receiving signals from the communicator 160, and provide the signals to the user through the interface module included in the external device 20. In addition, when the controller 140 receives blood pressure measurement information from the external device 20 through the communicator 160, the controller 140 may provide the information to the user through the display 150.

Figure 10:
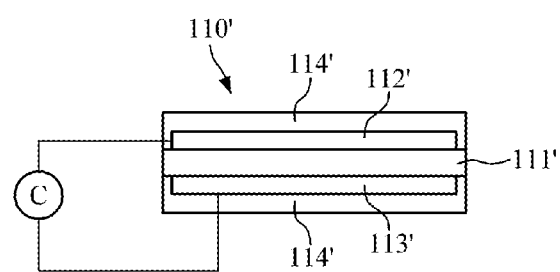
FIG. 10 is a cross-sectional view illustrating another example of a touch sensor.

FIG. 10 is a cross-sectional view illustrating another example of the touch sensor.

Referring to FIG. 10, the touch sensor 110' may include a first transparent electrode 112' and a second transparent electrode 113' which are disposed on a top surface and a bottom surface of a transparent substrate 111', respectively. The first and second transparent electrodes 112' and 113' may be covered by transparent covers 114'. In this case, the transparent substrate 111' may be formed of transparent plastic or transparent glass to have optical transparency and an insulation property. The transparent substrate 111' supports the first and second transparent electrodes 112' and 113'.

The first and second transparent electrodes 112' and 113' may be formed of a transparent conductive material, such as ITO or a carbon nanotube, on the top surface and the bottom surface of the transparent substrate 111', respectively. The first and second transparent electrodes 112' and 113' may be each formed with a constant thickness on the top surface and the bottom surface of the transparent substrate 111', respectively. The first transparent electrode 112' may act as a ground electrode and the second transparent electrode 113' may act as a sensing electrode.

The transparent covers 114' may be made of transparent plastic or transparent glass to have optical transparency and an insulation property. The transparent covers 114' protect the first and second transparent electrodes 112' and 113'. Although not illustrated, the second transparent electrode 113' may be formed on an additional transparent substrate. In this case, the transparent cover 114' which covers the second transparent electrode 113' may be omitted.

Like the touch sensor 110 in the example illustrated in FIG. 2, the touch sensor 110' in the present example measures a contact area of the finger 10 based on an amount of change in the capacitance between the first transparent electrode 112' and the second transparent electrode 113' according to the contact of the finger 10.

Figure 11A:
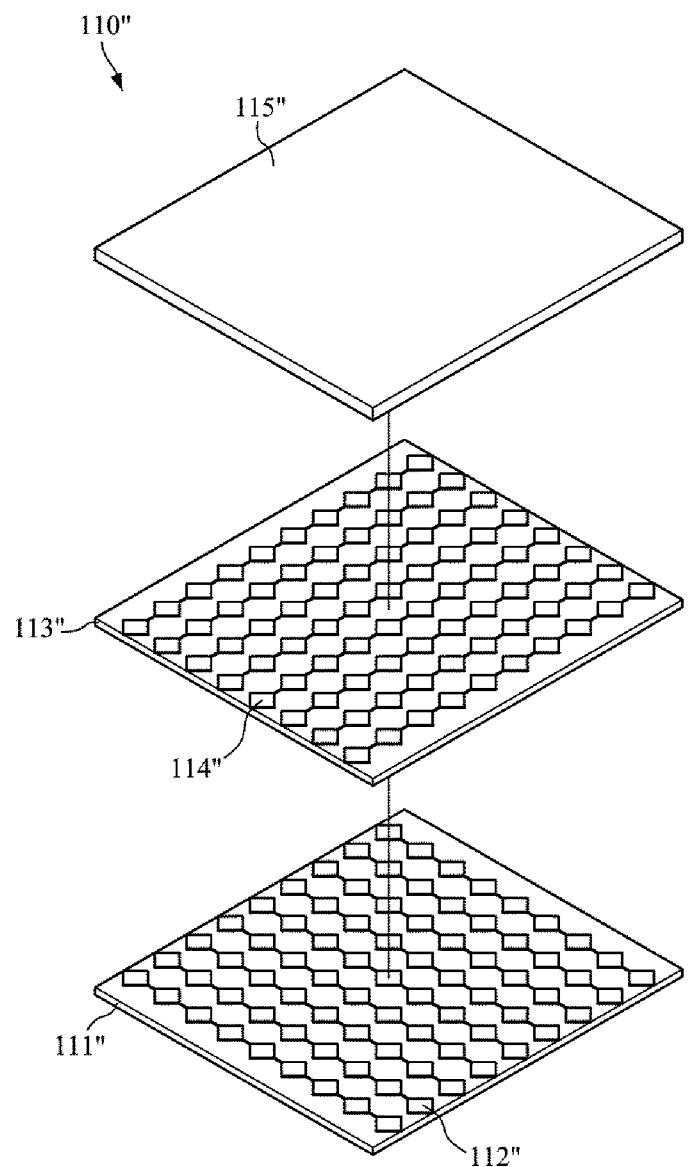
FIG. 11A is an exploded perspective view illustrating another example of the touch sensor.
Figure 11B:
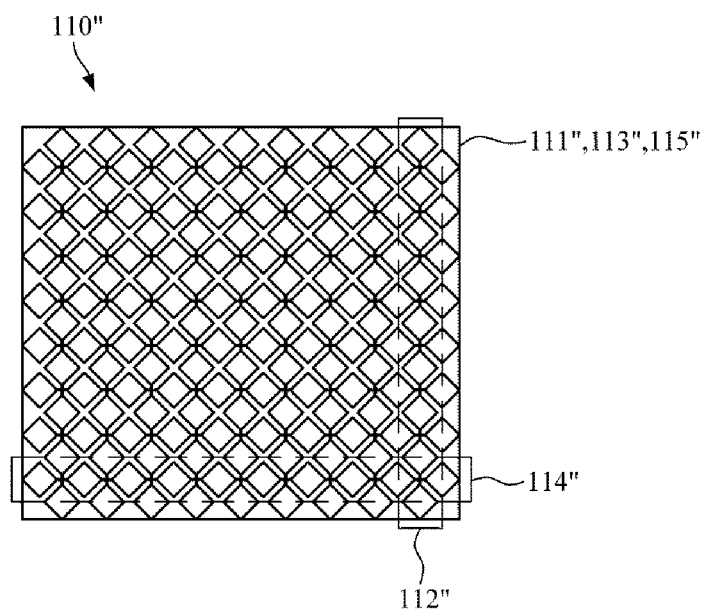
FIG. 11B is a plan view of FIG. 11A.

FIG. 11A is an exploded perspective view illustrating another example of the touch sensor. FIG. 11B is a plan view of FIG. 11A.

Referring to FIGS. 11A and 11B, a touch sensor 110" includes a transparent substrate 111", sensing lines 112" formed on the transparent substrate 111" and arranged in a plurality of rows, a transparent insulating layer 113" covering the sensing lines 112", driving lines 114" formed on the transparent insulating layer 113" and arranged in a plurality of columns, and a transparent cover 115" covering the driving lines 114".

The transparent substrate 111" may be made of transparent plastic or transparent glass to have optical transparency and an insulation property. The transparent substrate 111" supports the sensing lines 112".

The sensing lines 112" and the driving lines 114" may be made of a transparent conductive material, such as ITO, a carbon nanotube, or the like. The sensing lines 112" and the driving lines 114" may be arranged to cross each other and form a lattice structure. Intersection points between the sensing lines 112" and the driving lines 114" may each have coordinates.

The sensing lines 112" may be formed in a structure in which electrode pads are connected to each other by bridges. In this case, the electrode pads are each formed in a rhombic shape. The bridges have a significantly narrower width than that of the electrode pads. In the same manner as the sensing lines 112", the driving lines 114" may also be formed in a structure in which electrode pads are connected to each other by bridges. The sensing lines 112" and the driving lines 114" may be arranged such that the bridges thereof cross each other. Therefore, two electrode pads of the sensing line 112" and two electrode pads of the driving line 114" may be arranged around each intersecting point of the bridges.

The transparent insulating layer 113" insulates the sensing lines 112" and the driving lines 114". The transparent insulating layer 113" is formed of a material having optical transparency and an insulation property.

The transparent cover 115" may be made of transparent plastic or transparent glass to have optical transparency and an insulation property. The transparent cover 115" protects the driving lines 114". The transparent cover 115" may be adhered to the transparent insulating layer 113" by an adhesive layer while covering the driving lines 114".

The touch sensor 110" measures the contact area of the finger 10 in the following manner. When the user touches an upper portion of the transparent cover 115" with a finger of the user in a standby state in which a sensing current is sequentially provided to the driving lines 114", a change of capacitance occurs at intersecting points in contact with the finger among the intersecting points between the sensing lines 112" and the driving lines 114". In this case, among the intersecting points at which the change of capacitance occurs, coordinates of the outermost intersecting points may be obtained and the contact area of the finger 10 may be calculated based on the obtained coordinate information.

Signals output from the driving lines 114" and the sensing lines 112" may be processed by a signal processor dedicated for the touch sensor and then provided to the controller 140. The controller 140 sequentially provides a sensing current to the driving lines 114". In this state, when the user touches the touch sensor 110" with a finger, the controller 140 extracts intersecting points at which a change of capacitance occurs from among the intersecting points between the sensing lines 112" and the driving lines 114". The controller 140 obtains coordinates of the outermost intersecting points among the intersecting points at which the change of capacitance occurs, and calculates an area limited by the outermost intersecting points. The calculated area corresponds to the contact area of the finger 10.

Elements of the touch sensor 110", other than the sensing lines 112" and the driving lines 114", are not limited to the aforementioned examples, and may be configured in various ways as long as they can perform the above-described functions.

For example, the controller 140 may identify a user based on a user's fingerprint provided from the touch sensor 110". In this case, the touch sensor 110" illustrated in FIGS. 11A and 11B is used. The touch sensor 110" may obtain fingerprint information by recognizing differences in capacitance according to valley and ridge patterns of a fingerprint at intersecting points between the sensing lines 112" and the driving lines 114". Intervals between the sensing lines 112" and the driving lines 114" are set such that a fingerprint pattern can be sufficiently recognized.

The fingerprint information obtained from the touch sensor 110" is provided to the controller 140. The controller 140 compares the fingerprint information obtained from the touch sensor 110" with pieces of fingerprint data input in advance, thereby identifying the user. The controller 140 may have stored blood pressure information measured from the user in a storage device as the pertinent user information.

A blood pressure of a user may be taken into account by a height, a weight, and/or an age of the user or the like. In this case, the controller 140 may correct the blood pressure according to previously input information about the user's height, weight, and age. A blood pressure estimation correlation model suitable for each user is stored in the storage device in advance, and the controller 140 may correct the blood pressure by selecting a blood pressure estimation correlation model suitable for the pertinent user from the storage device.

Figure 12:
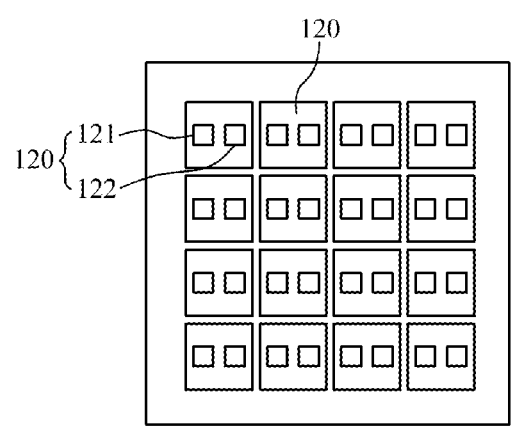
FIG. 12 is a plan view illustrating another example of a photoplethysmogram (PPG) sensor.

FIG. 12 is a plan view illustrating another example of the PPG sensor.

Referring to FIG. 12, a plurality of PPG sensors 120 may be formed in an array. The PPG sensors 120 may be arranged in a plurality of rows along horizontal and vertical axes in a lattice form.

The controller 140 may extract a PPG signal from the PPG sensor 120 provided at a contact center based on a contact location signal generated by the touch sensor 110". Therefore, the controller 140 may achieve a more accurate blood pressure by extracting an optimal PPG signal. In another example, the controller 140 may extract PPG signals from the PPG sensors 120 using a time-division method, and then select an optimal PPG signal therefrom, thereby achieving a more accurate blood pressure.

Figure 13:
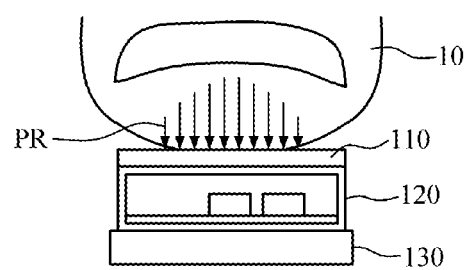
FIG. 13 is a diagram for describing an example of correction of contact pressure.

As illustrated in FIG. 13, the controller 140 may create a contact pressure profile PR according to a contact region, based on a contact area signal and a touch force signal, and then correct the contact pressure exerted on the user's blood vessel based on the contact pressure profile PR. In this case, the touch sensor 110" illustrated in FIGS. 11A and 11B may be used. The touch sensor 110" outputs a capacitance value differently depending on the degree of contact at the intersecting points between the sensing lines 112" and the driving lines 114". The controller 140 may create a contact pressure profile PR according to a contact region based on the capacitance values provided from the touch sensor 110" and correct the contact pressure.

Figure 14:
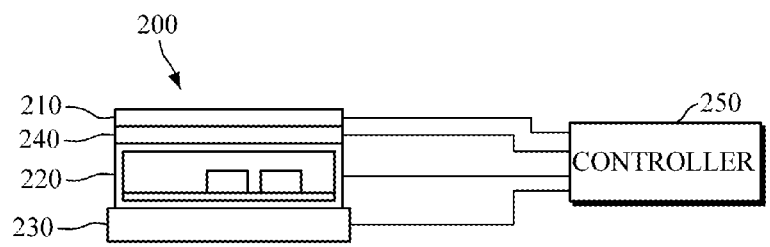
FIG. 14 is a diagram illustrating a configuration of the touch-type blood pressure measurement apparatus according to a second example embodiment.

FIG. 14 is a diagram illustrating a configuration of the touch-type blood pressure measurement apparatus according to a second example embodiment.

Referring to FIG. 14, the touch-type blood pressure measurement apparatus 200 according to the second example embodiment includes a touch sensor 210, a PPG sensor 220, a force sensor 230, a temperature sensor 240, and a controller 250. The touch sensor 210, the PPG sensor 220, and the force sensor 230 may be configured to be the same as the touch sensor 110, 110', or 110", the PPG sensor 120, and the force sensor 130 of the first example embodiment, respectively.

The temperature sensor 240 measures a temperature of a finger in contact with the touch sensor 210 to generate a temperature signal. The temperature sensor 240 may be disposed between the touch sensor 210 and the PPG sensor 220. The temperature sensor 240 may have optical transparency to transmit light emitted from the PPG sensor 220 to the finger 10 and to transmit light reflected from a tissue of the finger 10 to the PPG sensor 220. The temperature sensor 240 may include a thermocouple.

A PPG signal may be affected by temperature. In this case, the controller 250 may correct a PPG signal according to the temperature signal generated by the temperature sensor 240. The controller 250 may correct the PPG signal according to the temperature signal based on a correlation model that indicates a correlation between a temperature stored in a storage device and a PPG signal. Accordingly, the controller 250 may achieve a more accurate blood pressure based on the corrected PPG signal.

A signal output from the temperature sensor 240 may be processed by a signal processor dedicated for the temperature sensor and then a resulting signal may be provided to the controller 250. When the signal processor receives the signal from the temperature sensor 240, the signal processor may perform preprocessing, such as noise removal from the received signal, signal amplification, or the like, and convert the signal into a digital signal if the received signal is an analog signal.

Figure 15:
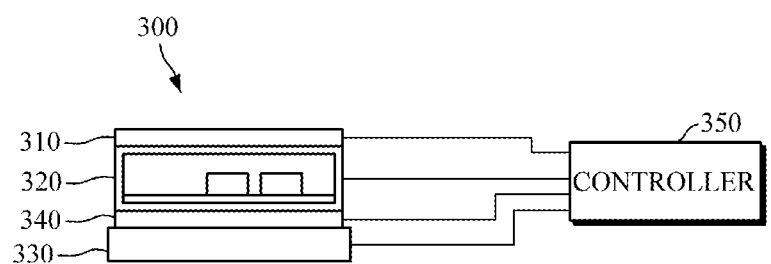
FIG. 15 is a diagram illustrating a configuration of the touch-type blood pressure measurement apparatus according to a third example embodiment.

FIG. 15 is a diagram illustrating a configuration of the touch-type blood pressure measurement apparatus according to a third example embodiment.

Referring to FIG. 15, the touch-type blood pressure apparatus 300 according to the third example embodiment includes a touch sensor 310, a PPG sensor 320, a force sensor 330, a contact pressure adjuster 340, and a controller 350.

The touch sensor 310, the PPG sensor 320, and the force sensor 330 may be configured to be the same as the touch sensor 110, 110', or 110", the PPG sensor 120, and the force sensor 130 in the first example embodiment, respectively. The contact pressure adjuster 340 is provided to adjust a contact pressure exerted on the touch sensor 310 by the user. The contact pressure adjuster 340 may be disposed between the PPG sensor 320 and the force sensor 330. The contact pressure adjuster 340 may adjust the contact pressure exerted on the touch sensor 310 by the user by moving the PPG sensor 320 to cause the touch sensor 310 to move relative to the finger 10.

The controller 350 controls the contact pressure adjuster 340 such that a contact pressure of a predetermined pattern is applied to the touch sensor 310. For example, when the user touches and removes a finger of the user from the touch sensor 310 for blood pressure measurement, the controller 350 may control the contact pressure adjuster 340 so that the contact pressure is applied to the touch sensor 310 in the pattern of the guideline GL shown in FIG. 8. Consequently, more accurate blood pressure measurement may be realized.

The contract pressure adjuster 340 may be formed by a piezoelectric actuator or a voice coil motor. The piezoelectric actuator is configured such that mechanical displacement is caused by an inverse piezoelectric effect when potential difference is applied thereto. The voice coil motor is configured such that a magnet which generates a magnetic field is arranged to face a current-supplied coil to create the Lorentz force acting perpendicular to the direction of the magnetic field and the current, thereby causing mechanical displacement of a moving object.

Figure 16:
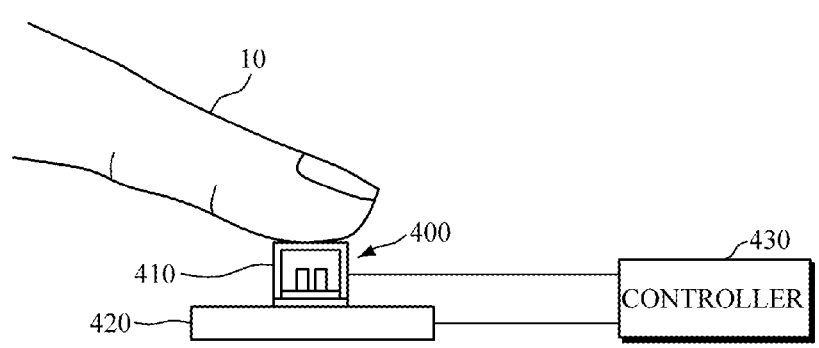
FIG. 16 is a diagram illustrating a configuration of the touch-type blood pressure measurement apparatus according to a fourth example embodiment.

FIG. 16 is a diagram illustrating a configuration of the touch-type blood pressure measurement apparatus according to a fourth example embodiment.

Referring to FIG. 16, the touch-type blood pressure measurement apparatus 400 according to the fourth example embodiment includes a PPG sensor 410, a force sensor 420, and a controller 430.

The PPG sensor 410 measures a PPG signal of the user while a finger 10 is in contact with the PPG sensor 410. Like the example shown in FIG. 1, the PPG sensor 410 may include one light source and one photodetector. Alternatively, a plurality of PPG sensors 410 may be formed in an array, like the example shown in FIG. 12.

The user may touch a predetermined contact area of the PPG sensor 410 with a finger 10 of the user. The predetermined contact area corresponds to an area of light transceiving region of the PPG sensor 410, for example, an upper area of the PPG sensor 410. An upper portion of the PPG sensor 410 may be formed to be smaller than the tip of the finger 10. Here, the upper area of the PPG sensor 410 is set such that the constant area is constant even when a touch force applied to the PPG sensor 410 varies.

The force sensor 420 measures a touch force of the finger 10 in contact with the PPG sensor 410. The force sensor 420 may be configured to be the same as the force sensor 130 of the first example embodiment.

The controller 430 obtains a blood pressure of the user based on the measured PPG signal, the touch force signal, and predetermined contact area information. For example, the controller 430 calculates a contact pressure based on the predetermined contact area information and the measured touch force signal. In this case, the controller 430 may calculate an average contact pressure by dividing the touch force value by the predetermined contact area.

The controller 430 obtains the user's blood pressure from a change of the PPG signal according to the calculated contact pressure. In this case, like in the example described above, the controller 430 estimates that the contact pressure corresponding to the maximum amplitude between a DBP and an SBP is an average blood pressure and estimate the DBP and the SBP at the maximum amplitude.

Figure 17:
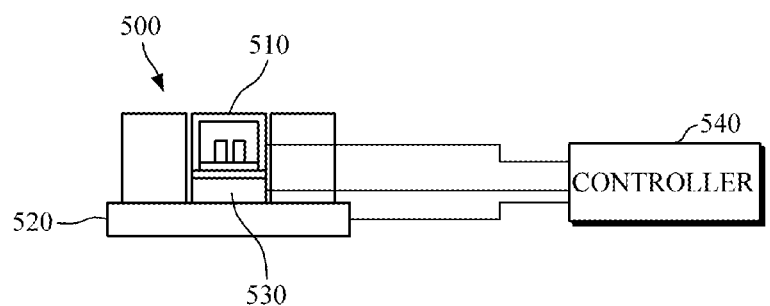
FIG. 17 is a diagram illustrating a configuration of the touch-type blood pressure measurement apparatus according to a fifth example embodiment.

FIG. 17 is a diagram illustrating a configuration of the touch-type blood pressure measurement apparatus according to a fifth example embodiment.

Referring to FIG. 17, the touch-type blood pressure measurement apparatus 500 according to the fifth example embodiment includes a PPG sensor 510, a force sensor 520, a contact pressure adjuster 530, and a controller 540.

The PPG sensor 510 may be configured to be the same as the PPG sensor 410 of the fourth example embodiment. The force sensor 520 may be configured to be the same as the force sensor 130 of the first example embodiment. The contact pressure adjuster 530 is provided to control a contact pressure exerted on the PPG sensor 510 by the user. That is, the contact pressure adjuster 530 may adjust the contact pressure exerted on the PPG sensor 510 by the user by moving the PPG sensor 510. The contact pressure adjuster 530 may be configured to be the same as the contact pressure adjuster 340 of the third example embodiment. The controller 540 controls the contact pressure adjuster 530 so that a contact pressure of a predetermined pattern is applied to the PGG sensor 510.

Figure 18:
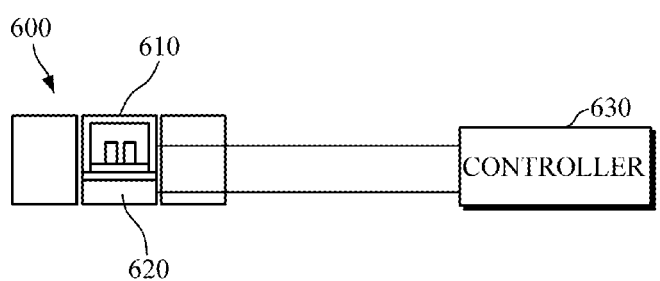
FIG. 18 is a diagram illustrating a configuration of the touch-type blood pressure measurement apparatus according to a sixth example embodiment.

FIG. 18 is a diagram illustrating a configuration of the touch-type blood pressure measurement apparatus according to a sixth example embodiment.

Referring to FIG. 18, the touch-type blood pressure measurement apparatus 600 according to the sixth example embodiment includes a PPG sensor 610, a contact pressure adjuster 620, and a controller 630.

The PPG sensor 610 measures a PPG signal of the user while a finger 10 of the user is in contact with the PPG sensor 610. The PPG sensor 610 may be configured to be the same as the PPG sensor 410 of the fourth example embodiment.

The contact pressure adjuster 620 is provided to adjust a contact pressure exerted on the PPG sensor 610 by the user. The contact pressure adjuster 620 may include an actuator and a force sensor. The actuator may be a piezoelectric actuator or a voice coil motor. The actuator is controlled by the controller 630 based on the contact area and a touch force signal measured by the force sensor.

The controller 630 and continuously obtains a user's blood pressure by controlling the contact pressure adjuster 620 to adjust the contact pressure and analyzing a change of the PPG signal according to the adjustment of the contact pressure.

Figure 19:
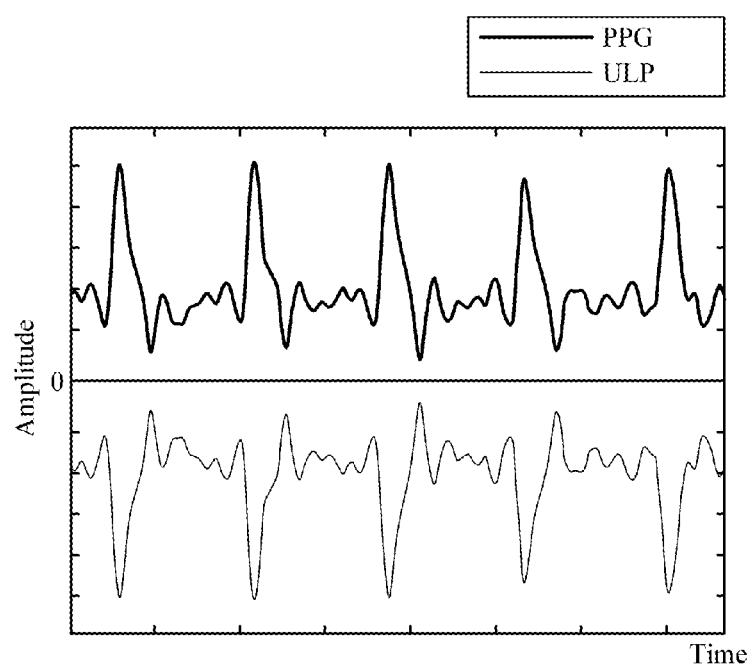
FIG. 19 is a graph for describing a blood pressure measurement process of FIG. 18.

For example, as shown in FIG. 19, the controller 630 generates a contact pressure signal ULP using the contact pressure adjuster 620 so as to cancel out the PPG signal generated by the PPG sensor 610. Then, the controller 630 may continuously obtain a blood pressure based on the contact pressure that cancels out the PPG signal.

That is, the controller 630 may control the contact pressure using the contact pressure adjuster 620 and continuously obtain the blood pressure using a vascular unloading or volume clamp technique. In this case, since the PPG signal is a waveform that reflects a blood pressure, a value obtained by inverting the contact pressure signal ULP that cancels out the PPG signal may be estimated as a blood pressure. The controller 630 may display the blood pressure through the display 150, allowing the user to monitor the blood pressure.

Figure 20:
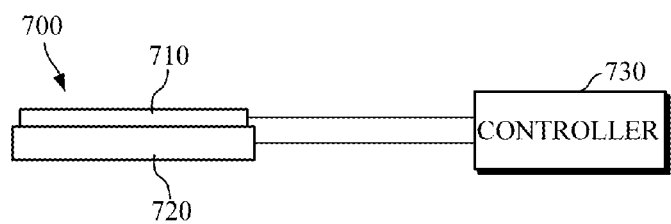
FIG. 20 is a diagram illustrating a configuration of the touch-type blood pressure measurement apparatus according to a seventh example embodiment.

FIG. 20 is a diagram illustrating a configuration of the touch-type blood pressure measurement apparatus according to a seventh example embodiment.

Referring to FIG. 20, the touch-type blood pressure measurement apparatus 700 according to the seventh example embodiment includes a touch sensor 710, a force sensor 720, and a controller 730.

The touch sensor 710 measures a contact area signal when the user's finger 10 is in contact with the touch sensor 710. The touch sensor 710 may be configured as one of touch sensors 110, 110', and 110" in the aforementioned examples. The force sensor 720 measures a touch force signal of the finger 10 in contact with the touch sensor 710. The force sensor 720 may be configured as the force sensor 130 of the first example embodiment.

The controller 730 obtains a user's blood pressure based on the measured contact area signal and the touch force signal. For example, the controller 730 may acquire the amplitude of a pulse and the touch force signal by analyzing the signal output from the force sensor 720 and estimate that a contact pressure at the maximum amplitude of the pulse is a blood pressure.

Specifically, the pulse transferred through the body may not only be measured through an optical signal, such as a PPG signal, but also be detected by measuring mechanical vibration. The mechanical vibration may be measured by the force sensor 720. The amplitude of the pulse obtained through measurement of mechanical vibration is affected by the contact pressure and the pattern thereof is similar to the PPG signal. Therefore, by using an AC component and a DC component of the touch force signal obtained by the force sensor 720 and the contact area signal obtained by the touch sensor 710, it is possible to measure a blood pressure in the same manner as the first example embodiment.

A number of example embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, it is understood that other implementations are within the scope of the following claims.

What is claimed is:

1. A touch-type blood pressure measurement apparatus comprising:
   a touch sensor configured to generate a contact area signal indicating a size of a contact area between the touch sensor and a finger of a user, when the finger of the user is in contact with the touch sensor;
   at least one photoplethysmogram (PPG) sensor configured to generate a PPG signal of the user while the finger is in contact with the touch sensor;
   a force sensor provided separately from the touch sensor and configured to generate a touch force signal of the finger in contact with the touch sensor, the touch force signal comprising a value of a force exerted by the finger to the force sensor; and
   a controller configured to determine a contact pressure based on the size of the contact area and the value of the force, and obtain a blood pressure of the user based on a change of the PPG signal according to the contact pressure, wherein the at least one PPG sensor is disposed between the touch sensor and the force sensor in a vertical direction of the touch-type blood pressure measurement apparatus.

2. The touch-type blood pressure measurement apparatus of claim 1, wherein the controller is further configured to generate a contact pressure profile according to a contact region based on the contact area signal and the touch force signal, and correct the contact pressure exerted on a blood vessel of the user based on the contact pressure profile.

3. The touch-type blood pressure measurement apparatus of claim 1, wherein the touch sensor comprises:
   a transparent substrate;
   a first transparent electrode disposed on the transparent substrate;
   a pair of second transparent electrodes disposed on the transparent substrate and spaced apart from the first transparent electrode to allow the first transparent electrode to be positioned between the pair of second transparent electrodes; and
   a transparent cover disposed to cover the pair of second transparent electrodes and expose the first transparent electrode,
   wherein the touch sensor is further configured to measure the size of the contact area based on an amount of change in capacitance between the first transparent electrode and the pair of second transparent electrodes, when the first transparent electrode and the pair of second transparent electrodes are contacted by the finger.

4. The touch-type blood pressure measurement apparatus of claim 1, wherein the at least one PPG sensor comprises a plurality of PPG sensors arranged in an array, and wherein the controller is further configured to identify one of the plurality of PPG sensors that is placed at a contact center among the plurality of PPG sensors, based on a contact location signal generated by the touch sensor, and obtain the PPG signal from the one of the plurality of PPG sensors that is identified as being placed at the contact center.

5. The touch-type blood pressure measurement apparatus of claim 1, wherein the at least one PPG sensor is disposed between the touch sensor and the force sensor in a vertical direction of the touch-type blood pressure measurement apparatus, and wherein a contact surface of the touch sensor configured to be in contact with the finger extends in a horizontal direction of the touch-type blood pressure measurement apparatus.

6. The touch-type blood pressure measurement apparatus of claim 1, further comprising a display configured to display the contact pressure of the finger in contact with the touch sensor and a guide for the user to apply the contact pressure in a predetermined pattern to the touch sensor.

7. The touch-type blood pressure measurement apparatus of claim 1, further comprising a temperature sensor configured to generate a temperature signal of the finger in contact with the touch sensor.

8. The touch-type blood pressure measurement apparatus of claim 7, wherein the controller is further configured to correct the PPG signal according to the temperature signal generated by the temperature sensor.

9. The touch-type blood pressure measurement apparatus of claim 1, wherein the touch sensor is further configure to obtain fingerprint information of the user, and the controller is further configured to identify the user based on the fingerprint information.

10. The touch-type blood pressure measurement apparatus of claim 9, wherein the controller is further configured to correct the blood pressure according to previously input information about at least one of a height, a weight, and an age of the user.

11. The touch-type blood pressure measurement apparatus of claim 1, further comprising a contact pressure adjuster configured to adjust the contact pressure applied to the touch sensor by the finger.

12. The touch-type blood pressure measurement apparatus of claim 11, wherein the controller is further configured to control the contact pressure adjuster so that the contact pressure is applied to the touch sensor in a predetermined pattern.

13. The touch-type blood pressure measurement apparatus of claim 11, wherein the contact pressure adjuster comprises a piezoelectric actuator or a voice coil motor.

14. The touch-type blood pressure measurement apparatus of claim 1, further comprising a contact pressure adjuster configured to adjust the contact pressure of the finger applied to the contact area by the finger by moving the at least one PPG sensor relative to a position of the finger.

15. A touch-type blood pressure measurement apparatus comprising:

a touch sensor configured to generate a contact area signal indicating a size of a contact area between the touch sensor and a finger of a user, when the finger of the user is in contact with the touch sensor;

a photoplethysmogram (PPG) sensor configured to generate a PPG signal of the user while the finger of the user is in contact with the PPG sensor;

a force sensor provided separately from the touch sensor and configured to generate a touch force signal of the finger in contact with the touch sensor, the touch force signal comprising a value of a force exerted by the finger to the force sensor;

a contact pressure adjuster comprising an actuator and configured to move the PPG sensor relative to a position of the finger to adjust a contact pressure applied to the PPG sensor by the finger; and a controller configured to continuously obtain a blood pressure of the user based on the size of the contact area, the PPG signal, and the value of the force, by controlling the contact pressure adjuster to move the PPG sensor relative to the position of the finger and thereby to adjust the contact pressure to have a predetermined pattern, and analyzing a change of the PPG signal according to adjustment of the contact pressure, wherein the PPG sensor is disposed between the touch sensor and the force sensor in a vertical direction of the touch-type blood pressure measurement apparatus, and wherein a contact surface of the touch sensor configured to be in contact with the finger extends in a horizontal direction of the touch-type blood pressure measurement apparatus.

16. The touch-type blood pressure measurement apparatus of claim 15, wherein the controller is further configured to continuously obtain the blood pressure of the user based on the contact pressure that is adjusted by the contact pressure adjuster to cancel out the PPG signal measured from the PPG sensor.

17. A method of measuring blood pressure of a touch-type blood pressure measurement apparatus comprising a touch sensor and a force sensor, the method comprising:

generating a contact area signal comprising a size of a contact area between the touch sensor and a finger of a user, when the finger of the user is in contact with the touch sensor;

generating a photoplethysmogram (PPG) signal of the user while the finger is in contact with the touch sensor;

generating, by the force sensor provided separately from the touch sensor, a touch force signal of the finger in contact with the touch sensor, the touch force signal comprising a value of a force exerted by the finger to the force sensor;

determining a contact pressure based on the size of the contact area and the value of the force; and obtaining a blood pressure of the user based on a change of the PPG signal according to the contact pressure wherein the at least one PPG sensor is disposed between the touch sensor and the force sensor in a vertical direction of the touch-type blood pressure measurement apparatus.

18. The method of claim 17, wherein the obtaining the blood pressure of the user comprises:

generating a contact pressure profile according to a contact region based on the contact area signal and the touch force signal, and correcting the contact pressure exerted on a blood vessel of the user based on the contact pressure profile.

19. The method of claim 17, further comprising displaying the contact pressure of the finger in contact with the touch sensor and a guide for the user to apply the contact pressure in a predetermined pattern to the touch sensor.

20. The method of claim 17, further comprising correcting the PPG signal according to a temperature of the finger in contact with the touch sensor.

* * * * *